United States Patent [19]

Pambianchi et al.

[11] Patent Number: 5,733,300
[45] Date of Patent: *Mar. 31, 1998

[54] SINGLE USE, BI-DIRECTIONAL LINEAR MOTION LANCET

[75] Inventors: Michael S. Pambianchi, New Milford, Conn.; Dominick F. Grube, Ogdensburg, N.J.

[73] Assignee: Array Medical, Inc., Somerville, N.J.

[*] Notice: The term of this patent shall not extend beyond the expiration date of Pat. No. 5,662,672.

[21] Appl. No.: 789,568

[22] Filed: Jan. 28, 1997

Related U.S. Application Data

[63] Continuation-in-part of Ser. No. 653,712, May 23, 1996, Pat. No. 5,662,672.

[51] Int. Cl.⁶ .................................................. A61B 17/14
[52] U.S. Cl. .................................................. 606/181; 606/182
[58] Field of Search .................................. 606/181, 182, 606/185, 189, 184

[56] References Cited

U.S. PATENT DOCUMENTS

| | | |
|---|---|---|
| 3,760,809 | 9/1973 | Campbell, Jr. . |
| 3,902,475 | 9/1975 | Begg et al. . |
| 4,078,552 | 3/1978 | Chen et al. . |
| 4,230,118 | 10/1980 | Holman et al. . |
| 4,414,975 | 11/1983 | Ryder et al. . |
| 4,539,988 | 9/1985 | Shirley et al. . |
| 4,553,541 | 11/1985 | Burns . |
| 4,580,565 | 4/1986 | Cornell et al. . |
| 4,643,189 | 2/1987 | Mintz . |
| 4,715,374 | 12/1987 | Maggio . |
| 4,844,095 | 7/1989 | Chiodo et al. . |
| 4,889,117 | 12/1989 | Stevens . |
| 4,892,097 | 1/1990 | Ranalletta et al. . |
| 4,983,178 | 1/1991 | Schnell . |
| 4,990,154 | 2/1991 | Brown et al. . |
| 5,026,388 | 6/1991 | Ingalz . |
| 5,074,872 | 12/1991 | Brown et al. . |
| 5,100,427 | 3/1992 | Crossman et al. . |
| 5,152,775 | 10/1992 | Ruppert . |
| 5,314,441 | 5/1994 | Cusack et al. . |
| 5,366,469 | 11/1994 | Steg et al. . |
| 5,366,470 | 11/1994 | Ramel . |
| 5,395,388 | 3/1995 | Schraga . |
| 5,421,347 | 6/1995 | Enstrom . |
| 5,439,473 | 8/1995 | Jorgensen . |
| 5,476,474 | 12/1995 | Davis et al. . |
| 5,514,152 | 5/1996 | Smith . |
| 5,611,809 | 3/1997 | Marshall et al. ............... 606/181 |

Primary Examiner—Michael Buiz
Assistant Examiner—Kevin Truong
Attorney, Agent, or Firm—Ralph T. Lilore

[57] ABSTRACT

A skin piercing device which converts a longitudinal linear motion of a blade within the housing of the device into a vertical linear motion which, in consequence of the placement of biasing member, restraints and stops in the device, results in the ejection of the blade out of the housing and into the patient's skin and back again into the housing in a rapid "in-out" fashion. The dimensions of the restraints and stop s are individually controllable and, as a result, it is possible to achieve a length of cut which is independent of the depth of cut.

18 Claims, 3 Drawing Sheets

SINGLE USE, BI-DIRECTIONAL LINEAR MOTION LANCET

This application is a continuation-in-part of U.S. Ser. No. 08/653,712 filed May 23, 1996 now U.S. Pat. No. 5,662,672.

BACKGROUND OF INVENTION

This invention relates to lancet devices of the kind used to produce incisions in the skin for the purpose of releasing small amounts of blood therefrom.

The prior art is replete with cutting devices used to make small incisions in the finger or some other accessible tissue of the patient. Many different types of lancet devices have been described, some of which have been commercialized. In general, they comprise cutting components located in a housing which conceals the cutting device and the actuating motion which causes the blade to be projected out of the housing and into the patient's tissue. Usually, the blade communicates with a restrained spring means and responds to the uncoiling action of the spring means upon release of the restraint. The blade then moves in a linear or a rotational motion through the housing and into the tissue site to be cut. Oftentimes, such devices are painful or inconvenient to use.

In the prior art, there exist many different designs for providing such incisions. Modern devices are usually designed for single-use, disposable operation and utilize a spring-loaded mechanism for accelerating the blade or needle through the course of its cutting motion. In general, three main types of lancet devices are encountered in the prior art. They may be classified as "stab", "slap", and "slice" devices.

The simplest of these is the "stab" group, to which the majority of prior art devices belongs. Devices of this group, exemplified by U.S. Pat. No. 4,889,117 issued on Dec. 26, 1989 to Stevens entitled DISPOSABLE LANCET and U.S. Pat. No. 4,553,541 issued to Burns entitled AUTOMATIC RETRACTABLE LANCET ASSEMBLY, employ a sharp, pointed needle or blade which is driven directly into the patient's skin with a puncturing action. The needle or blade may then be retracted back into its housing. Devices of this type have an advantage in their simplicity, though they cannot offer a completely controllable incision, nor do they attempt to address the needs of patients more susceptible to epidermal trauma, such as the elderly or the newborn.

Lancet devices of the "slap" group are similar in many ways to the "stab" group. For example, in U.S. Pat. No. 3,760,809 to Campbell, Jr. entitled SURGICAL LANCET HAVING CASING, a sharp blade is affixed to a flexible member inside the housing. In the starting position, this flexible member is bent at one end and hooked to the release mechanism at the roof of the housing. When activated, the energy stored in the flexible member is released, slapping the blade down through a sealed membrane and into the patient's skin. The incision produced is very similar to those produced by "stab" devices. Though they operate very quickly, both "stab" and "slap" devices produce an incision of nonreproduceable depth and can cause patient discomfort. Retracting the blade requires a complicated mechanism, or is not done at all in prior art devices of these types.

The third type of prior art device is the group characterized by blades which move primarily in a direction parallel to the skin of the patient, using a slicing motion to create an incision. In U.S. Pat. No. 5,314,441 to Cusack, et. al. entitled DISPOSABLE SLICING LANCET ASSEMBLY, a blade, sharpened only on one vertical edge, is attached to a fixed pivot point in the center of the housing. A torsional spring drives the rotating motion of the blade around this fixed pivot point, causing the blade to exit the housing, perform a slicing incision in the patient's skin, and then reenter the housing for the balance of its motion. Further, the path of the blade need not be purely circular; using an elongated slot in the blade, motion in the radial direction may also be accomplished. This allows the path of the blade to be specified precisely, by implementing a guide slot embossed on an interior wall of the housing. In U.S. Pat. No. 4,643,189 to Mintz entitled APPARATUS FOR IMPLEMENTING A STANDARDIZED SKIN INCISION, such a guide slot is used to create an incision of uniform length and depth for bleeding time applications.

The present invention belongs to the group of "slicing" lancet devices, and addresses the need for an even simpler, more painless incision method utilizing strictly linear blade motion.

SUMMARY OF THE INVENTION

In accordance with the present invention, there is provided a device which in its broad sense converts a longitudinal linear motion of a blade within the housing of a device into a vertical linear motion which in consequence of the placement of biasing means, restraints and stops in the device results in the ejection of the blade out of the housing and into the patient's skin and back again into the housing in a rapid "in-out" fashion. The dimensions of the restraints and stops are individually controllable and, as a result, it is possible to achieve a length of cut which is independent of the depth of cut.

The configuration of the blade is such that a slicing edge is presented in the direction of longitudinal movement of the blade point. When the blade's longitudinal movement through the device is converted to the perpendicular linear thrust as will be discussed in more detail below, the blade point pierces the skin in a vertical move and then continues in a longitudinal direction movement for a short duration causing a slicing of tissue. This is followed by a rapid withdrawal of the blade from the incision area as a result of certain restraints and stops provided in the housing of the device cooperating with the shape of the blade opposite the blade point. Stated another way, the slicing motion traverses only linear motion and it does so in two dimensions, one a longitudinal direction within the housing, and the other a perpendicular movement first piercing the patient's skin followed by another perpendicular motion as the blade retracts, all the while being under the influence of a longitudinal thrust.

In a broadly defined device of the invention, there is provided a housing with an internal channel therein. The channel has associated therewith a cam surface to provide a pathway for a cam follower having a blade point attached thereto which induces the blade point to traverse a vertical pathway derived from the longitudinal movement of the blade in the channel. A significant part of the invention is the provision of a "holder" which serves multiple purposes including that of holding the blade in a perpendicular position relative to the skin of the patient when the device is in use. The holder also provides means in the form of resilient members and restraints to maintain the blade in a linear motion instead of a rotational motion as the cam surface is traversed. The holder also provides biasing means which permit the movement of said blade out of the housing into the skin and then retraction back into the housing.

Broadly, the device of the present invention comprises a generally elongated, housing having an internal channel, a cutting blade-holding assembly (the holder) disposed within said channel and carrying a blade having a pointed end with a slicing edge for piercing and cutting tissue and an end opposite thereto, said blade disposed generally in a direction perpendicular to said channel, said blade and said assembly being movable in said channel between a cocked first retracted position, an extended piercing and cutting position, and a second retracted position wherein the second retracted position is downstream of the piercing position, biasing means in contact with said holding assembly and disposed to move said assembly in a longitudinal direction through said channel from said first cocked retracted position into said extended piercing position and then into said second retracted position, stop means associated with said housing, ejection, and retraction means associated with said end opposite said pointed end of said blade and with said holding assembly and said housing and whereby when said holding assembly is moved upon its longitudinal pathway said stop means cooperate with said ejection means and retraction means to convert the longitudinal movement of the blade into transverse movement of said blade out of said housing and into skin piercing position, followed by retraction of said blade back into said housing.

The stop means associated with the housing described in the previous paragraph is included as part of the cam surface which will provide the pathway for the blade point when the end opposite the blade point acts as a cam follower. For convenience, the end of the blade opposite the blade point is sometimes referred to herein as the proximal end while the blade point end is sometime referred to as the distal end.

The ejection and retraction means discussed above may include a configuration of the proximal end of the blade in the form of a wedge shape or arrowhead shape having an angled leading edge which engages the stop means on the cam surface and cooperates with the stop means to cause the transverse movement of the blade point out of the housing and into the skin. Under some circumstances, the proximal end need not have an angled leading edge as when for example the stop means has an appropriate angled edge. As will be described below, other aspects of the means for ejection and retraction are included in the blade holding assembly which allow the blade point to move vertically against a yieldable resistance caused by a biasing means in the holder which then causes a retraction when the stop means of the cam surface is surpassed.

In the descriptions which follow, two graphic embodiments of the invention are presented. These embodiments represent two variations in cam surfaces to show the versatility of the invention relative to the blade holder configuration and two variations in the blade holding assembly itself. In the first embodiment described below, the cam surface comprises two slots for receiving the cam follower portion of the blade which in the embodiment shown is wedge or arrowhead shaped providing an angled leading edge. Separating the slots is a solid stop which deflects the wedge shaped proximal end of the blade out of the first slot injecting the blade point into the skin during its traversal of the stop and then back up into the second slot.

In tracing the pathway of the blade point, beginning with the movement caused by the release of a biasing means from its energy storing state, one would find that in the longitudinal pathway, the blade-holding assembly carrying the blade first moves longitudinally through a generally elongated channel in the housing from its first retracted resting position.

When the blade point reaches slot means in the housing at the area used for piercing the patient (piercing slot means), the configuration of the end opposite the blade point enables cooperation with a restraint or stop (housing stop) placed in registration with said piercing slot means in the housing. This configuration is in the form of an angled leading edge, such as is provided by an arrowhead, which engages the housing stop, i.e. the end of the slot. This causes a pushing down of the blade into the housing and a continuing longitudinal slicing movement therethrough as the biasing means continues its expansion action. The blade is thus ejected through the slot means out of the housing in a direction generally perpendicular to the first longitudinal motion, piercing the skin in that perpendicular direction.

The depth of the piercing and the subsequent cut is a function of the length of the entire blade from the piercing point to the end of the angled leading edge. It continues a slight distance longitudinally in a straight line in the patient's tissue as determined by the length of the opposing housing stop as it encounters the angled edge and then retracts into a second slot means perpendicularly in the housing to a second retracted position by reason of the angled leading edge of the end opposite the blade point having reached the slot and being urged upwardly therein by the release of pressure on the restraining means in said holding assembly. It will be apparent that instead of providing an angled leading edge at the proximal end of the blade, the stop means itself could provide an angled surface to be met by the proximal end and the same purpose would be served. Alternately, both the proximal end and the stop means could have parallel angled edges which contact and slide over each other.

Generally, the elements of the device which permit the blade to traverse the path described are facilitated by the first slot means of the housing itself which permit the blade to remain retracted as it moves through the housing, ejection means comprising the wall (stop) and the opposing slot provided in the path of the point to permit ejection of the knife point to pierce the skin, resilient or biasing means in the holding assembly in contact with the blade holder and engaging the knife to urge it down into the piercing slot upon deformation and to retract it upon release of the deformation. Movement of the blade is facilitated by biasing means located longitudinally which move the blade-holding assembly through the housing. The blade holding assembly itself has resilient means such as a spring, a foam, or a rubbery elastomeric material controlling the location, placement, and movement of the blade within the assembly.

In the second embodiment illustrated herein, instead of the cam surface comprising slots with an intermediate stop, the stop is a protrusion lying in the pathway of the proximal end of the blade. On each side of the protruding stop there are linear recesses to accommodate the proximal end of the blade as will be seen more fully below. The recesses and the protrusion form a cam surface. In addition, a second embodiment of the blade holding assembly in the form of a "c" shaped holder is shown.

In tracing the longitudinal pathway of the distal blade point in the embodiment with the protruding stop, beginning with the movement caused by the release of a biasing means from its energy storing state, the blade-holding assembly carrying the blade first moves through the first recess from its first retracted resting position longitudinally through the channel (which may be generally elongated) in the housing. As the blade moves along the cam surface, the configuration of the proximal end enables cooperation with the protruding stop located on the cam surface in registration with the slot through which the distal blade point will pass to pierce the skin.

This proximal configuration may also be in the form of an angled, or wedge-shaped leading edge; such as is provided by an arrowhead, which engages the protrusion on the cam surface. The protrusion may also be wedge-shaped of meshing orientation to the angled leading edge of the proximal end of the blade. This causes a pushing down of the blade into the housing and a continuing longitudinal slicing movement therethrough as the biasing means continues its expansion action. The blade is thus ejected through the piercing slot means out of the housing in a direction generally perpendicular to the first longitudinal motion, piercing the skin in that perpendicular direction.

The depth of the piercing and the subsequent cut is a function of the length of the entire blade from the piercing point to the end of the angled leading edge. It continues a slight distance longitudinally in a straight line in the patient's tissue as determined by the length of the opposing protruding stop as it encounters the angled cutting edge and then retracts into a second recessed means perpendicularly in the housing to a second retracted position by reason of the angled leading edge of the end opposite the blade point having completed its traversal of the stop and being urged upwardly into the recess by the release of pressure on the restraining means in said holding assembly.

Again, in the embodiment just described, the elements of the device which permit the blade to traverse the path described are the first recessed means in the housing itself which permits the blade to remain retracted as it moves through the housing, ejection means comprising the protruding stop and the opposing slot provided in the path of the point to permit ejection of the blade point to pierce the skin, a first resilient or biasing means in the holding assembly in contact with the blade holder which deforms and permits the blade point to move into the piercing slot upon deformation and to retract it upon release of the deformation.

Movement of the blade is facilitated by biasing means located longitudinally which move the blade-holding assembly through the housing. The blade-holding assembly itself has a second resilient means in this embodiment which acts in conjunction with the first resilient means and various other restraints to maintain the thrust of the blade point in a vertical direction. This will become more apparent when consideration is given to the drawings.

DETAILED DESCRIPTION OF THE DRAWINGS AND PREFERRED EMBODIMENTS

Figure 1:
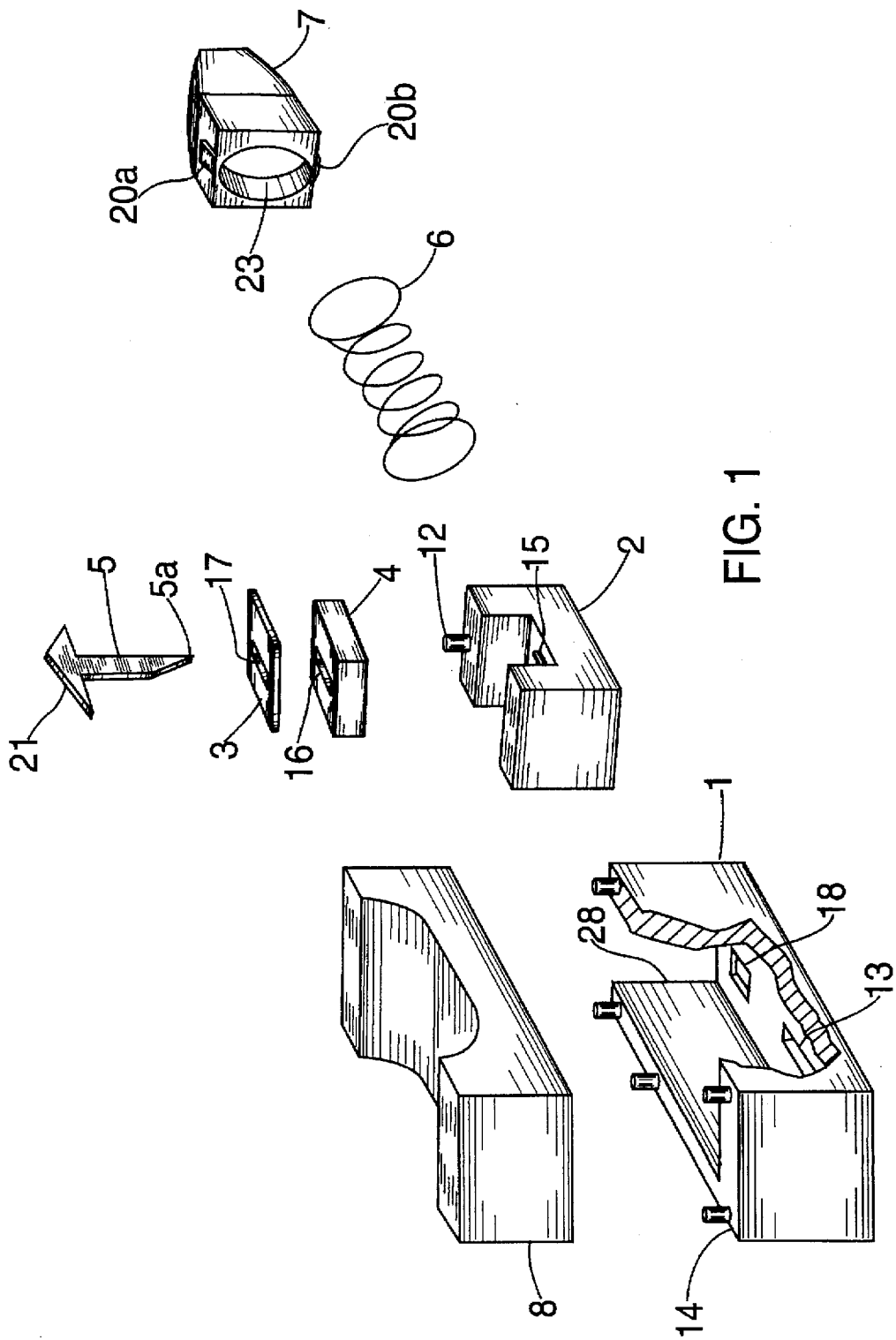
FIG. 1 is an exploded side view of the lancet device of the invention.

The device of FIG. 1 comprises an elongated slot 13 in the bottom surface of the housing 1 intended to be placed into contact with the skin to be pierced. When the device is activated, a cutting blade 5 will be ejected from the elongated slot 13, cut the patient's skin, and retract from the incision area back into the housing.

The cutting blade 5 having blade point 5a resides in the slot 17 of the cutting blade retaining means 3, an optional, but preferred component. The cutting blade retaining means 3 has a slot 17 from its top to its bottom surfaces and may be any shape consistent with the shape of the housing and the device itself. The angled leading edge head 21 (shown as part of the cutting blade 5) rests in slot 9a (FIG. 2) and sits against the top surface of the cutting blade retaining mean s 3. The leading edge 21 instead of terminating in the point of an arrowhead, may simply continue in a straight line colinear with the longitudinal direction of the housing or it may drop off into the main length of the blade after the desired length of the angled edge is traversed. As will be seen, head 21 constitutes part of the ejection means when in communication with stop 10 (FIG. 2) and part of the retraction means when stop 10 is traversed and slot 9b is reached. The cutting blade is held in the slot 16 running through the top and bottom surfaces of the resilient biasing means 4. As noted previously, the material used for the resilient biasing means 4 may be generally an elastomeric, resilient, "rubbery" material such as a silicone or other plastic polymeric material, rubber, a foam or spring means. Preferably, a rubbery material is used. Its purpose is to deform when the bottom of leading edge head 21 is pressed against blade retaining means 3 which in turn presses against resilient means 4 to allow point 5a to protrude from slot 13 and to force the blade to retract when the pressure on leading edge head 21 is released.

The cutting blade 5 resides in slot 15 of the blade carrier 2 (i.e. blade holding assembly or holder). The cutting blade 5 is designed not to protrude from the slot 15 in the blade carrier 2, when in the assembled state at rest. The blade carrier 2 generally conforms in shape to the channel 28 with a cut-out in its top surface, and has a slot 15 through the inner top surface of the cut-out to the bottom surface. A shear pin 12 is provided on carrier 2 protruding from its top surface. (One may also be provided on the bottom surf ace to provide stability.) The subassembly thus comprises cutting blade 5, preferably cutting blade retaining means 3, resilient means 4 which can act as a cutting blade retaining means via slot 16 itself, and blade carrier 2.

Figure 2:
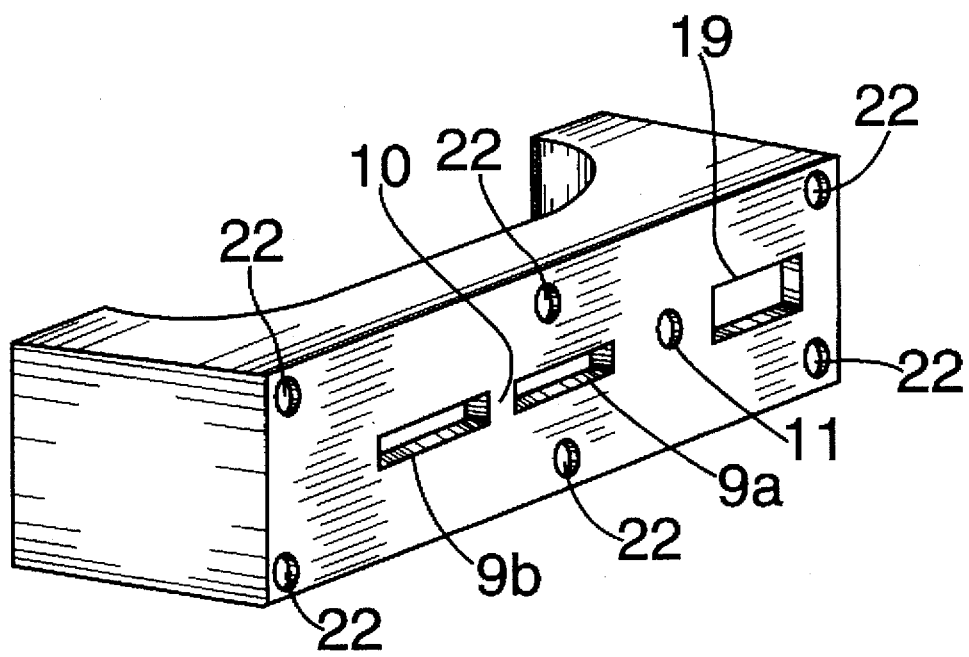
FIG. 2 is perspective view of the bottom of the top cover of FIG. 1.

The subassembly described above is placed against the bottom surface of the top cover 8 so that the shear pin 12 of the blade carrier 2 is accepted by the counterbore 11 of the top cover 8 (refer to FIG. 2). The top cover 8 of FIG. 2 has a cut-out in its top surface, counterbores 11 and 22 and slots 9a, 9b, and 19 in its bottom surface. The housing 1 mates with the top cover 8 so that the protruding pins 14 provided in the top surface of the housing press fit into the counterbores 22 of the top cover 8. Housing 1 (without the top cover 8), as shown, has a bottom surface, three sides, one open end 28 to accommodate blade carrier 2, and an open top to accommodate top cover 8. Housing 1 may, of course, be of a different shape such as a cylinder, for example. Elongated slots 13 and 18 are provided in its bottom surface. Spring biasing means 6 is placed into the open end of the mated housing 1 and top cover 8 and rests against the end surface of the blade carrier 2 previously inserted into 28. The final assembly step is to press the end cap 7 in the slot 18 of the housing 1 and the slot 19 of the top cover 8. The wedge-shaped protrusions 20a and 20b (FIG. 1) fit in slots 19 and 18, respectively, prevent the end cap 7 from being pushed out of the device by the linear spring biasing means 6 and hold the linear spring biasing means 6 in a semi-compressed state. The counterbore 23 in the end cap 7 accepts the linear spring biasing means 6 acting as a guide.

The function of the device is unique when compared to prior art devices. In use, the device is placed against the patient's skin with the elongated slot 13 of the housing 1 making contact with the skin. The operator of the device holds it between the thumb and index finger and uses the forefinger to press on the end cap 7. This pressure causes the shear pin 12 in the blade carrier 2 to break thereby acting as a triggering means for the expansion of the linear spring biasing means 6. The blade carrier 2 is then propelled longitudinally by the force of the linear spring biasing means 6. The leading edge 21 of the cutting blade 5 (which blade originally has its point residing in slot 9a), upon movement will contact the common section of wall 10 (stop) which acts as a stop between the two colinear slots 9a and 9b in the bottom surface of the top cover 8. This common section of wall 10, cooperating with lead edge 21, will force the cutting blade 5 transversely allowing it to eject first from the slot 15 in the blade carrier 2 and then from the slot 13 in the housing 1. The resulting deformation of the resilient means 4 will allow the "give" required for blade protrusion. The blade will make an incision in the skin and then be retracted back into the device when the barrier created by the common section of wall 10 is overcome by the leading edge head 21 of the cutting blade 5. The force required to retract the cutting blade 5 back into the device through slot 9b is provided by the resilient means 4. The device cannot be reset once the shear pin 12 has been broken making the device fully disposable with no chance of re-use.

In another embodiment, instead of providing peg 12 in the carrier to releasably secure the carrier to cover 8, a slot can be provided transversely through the carrier 2 located in registration with matching slots in the walls of housing 1 to receive means, such as a peg bolt or restraining rod which then act as the securing means. The carrier can then be projected into motion by either pushing or pulling the restraining rod out of the carrier. When in place, the carrier 2 would be in a cocked first retracted position. Release of the peg causes expansion of the spring means 6 triggering the required longitudinal movement of carrier 2. In addition, a biasing means 6 can be positioned in front of carrier 2 and appropriately connected and secured such that release of the carrier from the biasing means in an extended position causes a "pull" on said carrier.

Figure 3:
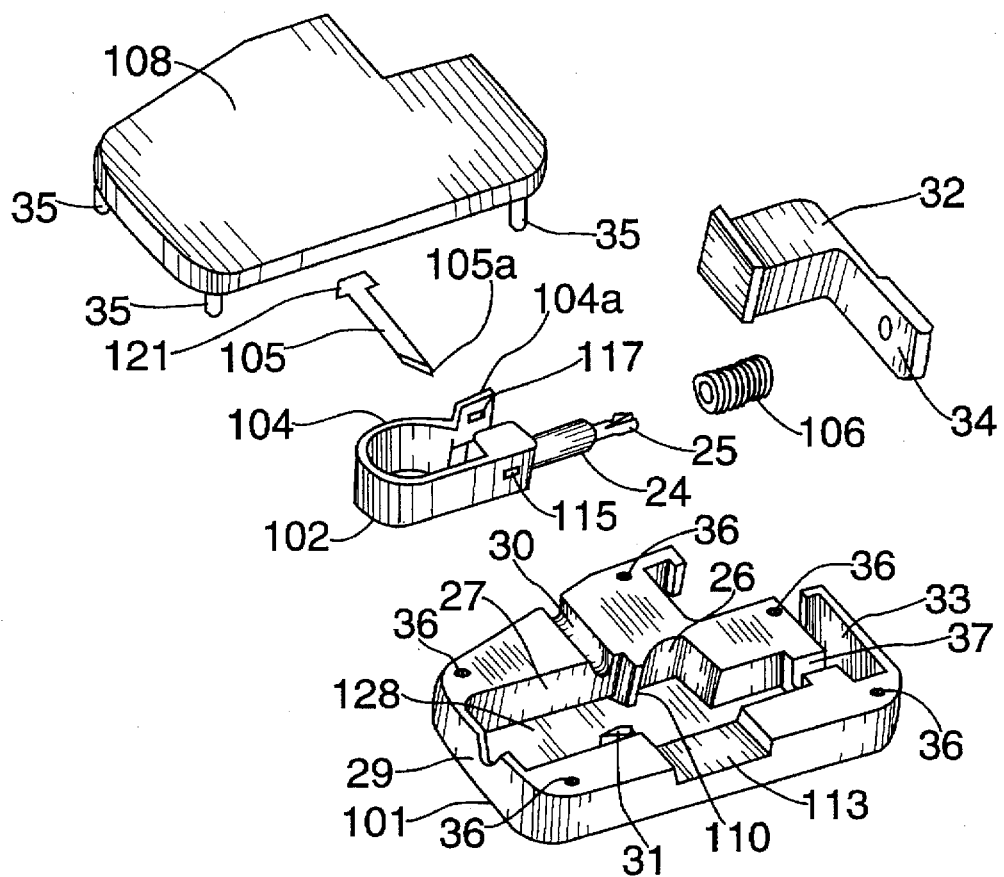
FIG. 3 is an exploded perspective view of a second embodiment of the invention.
Figure 4:
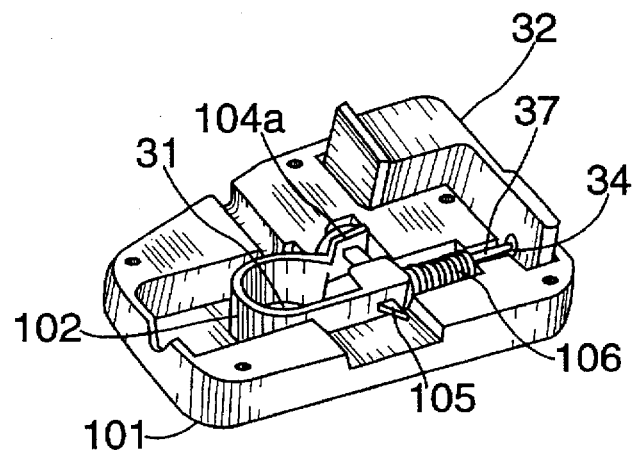
FIG. 4 is a view of the embodiment of FIG. 3 in assembled form with the top cover removed.

An additional embodiment of the present invention is illustrated in FIGS. 3 and 4. Elements illustrated in FIGS. 3 and 4 which correspond to the function of elements described above with respect to FIGS. 1 and 2 have been designated by corresponding reference numerals increased by one hundred. The embodiment of FIGS. 3–4 is designed for use in the same manner as the embodiment of FIGS. 1–2 unless otherwise stated.

The device of FIG. 3 comprises an elongated slot 113 in the bottom surface of the housing 101 intended to be placed into contact with the skin to be pierced. When the device is activated, a cutting blade 105 will be ejected from the elongated slot 113, cut the patient's skin, and retract from the incision area back into the housing 101.

The cutting blade 105 having blade point 105a resides in the slots 115 and 117 of the "c" shaped blade holder 102 (blade holding assembly) which comprises a "c" shaped section 104 as the resilient means which can be deformed and restored to its original position upon application of and removal of cam follower forces. The cutting blade 105 is designed not to protrude from the slot 115 in the blade holder 102 when in the assembled state at rest. The wedge-shaped head 121 of the cutting blade 105 sits on the top surface of the blade holder 102 at 104a with blade 105 in slots 117 and 115. The blade holder 102 generally conforms in shape to the channel 128 of the housing 101 with a slot 117 in its top surface and a slot 115 in its bottom surface. A shaft 24 accepts a spring-biasing means 106 and the tweezer-like end 25 of the shaft 24 aids in the triggering of the device, as will be seen. The material to be used for the blade holder 102 is generally an elastic material such as plastic, spring metal, rubber, elastomer and the like. The subassembly blade holder 102 thus comprises cutting blade 105, resilient means 104, cutting blade retaining means slots 117 and 115, and spring-biasing means 106.

The subassembly described above is placed in the channel 128 of the housing 101 so that the wedge-shaped head 121 of the cutting blade 105 resides against either surface 26 or surface 27 which are to either side of the wedge-shaped protrusion 110 (stop means) in the housing 101. (See FIG. 4 showing placement of blade holder 102 in the housing 101.) This option of placement considers the manufacturing qualities of the device. When placed against surface 26, the device is in the cocked position prior to the assembly of the top cover 108. When placed against surface 27, the device is in an uncocked state which can be loaded by machinery after the placement of the top cover 108. This can be accomplished by machinery pins which would access the blade holder 102 through the slots 29 and 30 in the housing 101. The optional elongated pin 31 in the housing 101 secures the blade holder 102 preventing any rocking motion of the blade holder 102 when the device is activated. The activation button 32 is placed in channel 33 of the housing 101. The activation button 32 has a conical recess 34 which also aids in the triggering of the device, as will be seen. The top cover 108 mates with the housing 101 so that the pins 35 of the bottom surface of the top cover 108 press fit into the counterbores 36 of the housing 101.

The function of the device is unique when compared to prior art devices. In use, the device is placed against the patient's skin, with the elongated slot 113 of the housing 101 making contact with the skin. The operator of the device holds it with the tip of the index finger on the activation button 32, the thumb on one side of the housing 101, and the remaining fingers on the other side of the housing 101. Forcing the activation button 32 into the housing 101 with the index finger will allow the conical recess 34 in the activation button 32 to engage the tweezer-like ends 25 of the shaft 24 on the blade holder 102 triggering the device by squeezing the ends of 25 toward each other and releasing the pressure that said ends exert on the edges of slot 37.

Alternately, the triggering can be accomplished by holding the top of the index or middle finger on the activation button 32 and the thumb on the side of the housing 101 opposite the activation button 32. Forcing the fingers toward each other will allow the conical recess 34 in the activation button 32 to engage the tweezer-like ends 25 of the shaft 24 of the blade holder 102 triggering the device. Triggering of the device allows for the uncoiling of the linear spring-biasing means 106. The blade holder 102 is then propelled longitudinally by the force of the linear spring-biasing means 106. The wedge-shaped head 121 of the blade 105 will contact the wedge-shaped protrusion or stop 110 upon movement creating the forces required to move the blade holder 102 away from the housing wall and force the cutting blade 105 to eject first from the slot 115 in the blade holder 102, and then from the slot 113 in the housing 101. In the embodiment shown, both the wedge-shaped protrusion 110 and the wedge-shaped head 121 are angled in the same direction relative to the longitudinal movement of blade holder 102 and have generally parallel surfaces in contact with each other, the edge of 121 sliding over the wedged surface of 110.

The elastic properties of the blade holder 102, especially the "c" section 104, allow the "give" required for blade 105 ejection. The blade 105 will make an incision in the skin and then be retracted back into the device when the barrier created by the two opposing wedge shapes 121 and 110 is overcome eliminating the separating forces described earlier. The force required to retract the cutting blade back into the device is provided by the elastic properties of the blade holder "c" section 104. This device accomplishes its incision without the pivoting action of the cutting blade and guided cam slots required by the prior art. In particular, slots 115 and 117 act as a retaining means against the tendency of blade 105 to pivot as "c" section 104 compresses. Part 104a, also of resilient elastic material (usually the same material as the "c" section), will flex as the blade 105 moves downwardly retained in a perpendicular position by slots 115 and 117 against the tendency of the blade otherwise to pivot.

A significant feature of this device is that any given point on the blade 105 will trace the same shaped pathway as any other point (although displaced in space) while the blade achieves both longitudinal and up-and-down motion simultaneously as it travels through the housing 101.

There are a variety of modifications that may be employed within the scope and spirit of the invention as will be apparent to those skilled in the art. All such modifications are intended to be encompassed within the scope of the invention.

We claim:

1. A disposable lancet skin piercing device comprising:
   a) a housing having an internal channel and an opening in said housing adapted to be placed on skin to be pierced,
   b) a blade-holding assembly disposed within said channel and carrying a blade having a pointed end and a slicing edge at said end for piercing and slicing skin and an end opposite thereto, said blade and said assembly being movable longitudinally in said channel from a cocked first retracted position to and through an extended piercing position, and then to a second retracted position wherein the second retracted position is downstream of the piercing position, said blade disposed generally in a direction perpendicular to said skin to be pierced,
   c) biasing means in contact with said blade-holding assembly and disposed to move said assembly in a longitudinal direction through said channel from said first cocked retracted position into said extended piercing position and into said second retracted position,
   d) stop means associated with said housing, and
   e) ejection means and retraction means associated with said blade and with said holding assembly,
whereby when said holding assembly is moved upon its longitudinal pathway said stop means cooperate with said ejection means and retraction means to convert the longitudinal movement of the blade into transverse movement of said blade out of said housing and into skin piercing position, followed by retraction of said blade back into said housing.

2. The device of claim 1 wherein the blade is held in a holding assembly comprising a resilient means capable of being compressed upon exertion of pressure thereon and of returning to substantially its original position when said pressure is released.

3. The device of claim 2 wherein said slicing edge is oriented in a slicing configuration relative to said skin and said ejection means comprises an angled leading edge head angled in the direction of longitudinal movement and located at the end opposite said blade point.

4. The device of claim 3 wherein the housing comprises a first elongated slot to accommodate at least a portion of said angled leading edge head when said device is in a cocked first retracted state, a second elongated slot downstream of said first slot and colinear therewith to accommodate at least a portion of said head in a second retracted state and as stop means a wall between said first and said second slots and colinear therewith, said wall being engageable with the angled leading edge of said head to induce a transverse component of motion to said blade when said head of said blade moves longitudinally and encounters said wall.

5. The device of claim 4 wherein opening in said housing is opposite to and in registration with said wall to accommodate the blade point when said head encounters said wall and moves transversely.

6. The device of claim 5 wherein said blade opening slot is greater in length in the longitudinal direction than the length of said wall in the same direction.

7. The device of claim 6 wherein the biasing means is spring activated.

8. The device of claim 7 wherein the spring biasing means is located upstream of the direction of longitudinal movement of said blade-holding assembly and said spring is in its energy storing state when the assembly is in the cocked first retracted state.

9. The device of claim 8 wherein said resilient means of said holding assembly is an elastomeric material.

10. The device of claim 2 wherein said ejection means comprises a cam follower surface on the blade at the end opposite said blade point said surface having a leading edge in the direction of longitudinal movement of said holding assembly from its first retracted position.

11. The device of claim 10 wherein the housing comprises a first recessed surface to accommodate said cam follower head when said device is in a cocked first retracted state, a second recessed surface downstream of said first recessed surface and colinear therewith to accommodate said cam follower head in a second retracted state and as stop means a protrusion between said first and said second recessed surfaces and colinear therewith, said protrusion being engageable with the cam follower head to induce a transverse component of motion to said blade when said cam follower head of said blade moves longitudinally and engages the recessed surfaces and protrusion.

12. The device of claim 11 wherein the protrusion has a surface angled in the direction of longitudinal movement of said assembly when said device is activated.

13. The device of claim 11 wherein said cam follower surface is angled in the direction of longitudinal movement upon activation.

14. The device of claim 13 wherein the protrusion has a surface angled in the direction of longitudinal movement of said assembly when said device is activated such that both the protrusion surface and the cam follower surface are generally parallel and contact each other when said device is activated.

15. The device of claim 14 wherein said opening in said housing is greater in length in the longitudinal direction than the length of said protrusion in the same direction.

16. The device of claim 15 wherein the biasing means is spring activated.

17. The device of claim 16 wherein the spring biasing means is located upstream of the direction of longitudinal movement of said blade-holding assembly and said spring is its energy storing state when the assembly is in the cocked first retracted state.

18. The device of claim 17 wherein said resilient means of said holding assembly is a plastic material.

* * * * *